United States Patent [19]

LaZonby et al.

[11] Patent Number: 5,658,467
[45] Date of Patent: Aug. 19, 1997

[54] METHOD AND COMPOSITION FOR INHIBITING GROWTH OF MICROORGANISMS INCLUDING PERACETIC ACID AND A NON-OXIDIZING BIOCIDE

[75] Inventors: Judy G. LaZonby, Crystal Lake; Robert E. McCarthy, Naperville; Nancy L. Casselman, Wheaton, all of Ill.

[73] Assignee: Nalco Chemical Company, Naperville, Ill.

[21] Appl. No.: 559,685

[22] Filed: Nov. 15, 1995

Related U.S. Application Data

[63] Continuation-in-part of Ser. No. 350,570, Dec. 7, 1994, Pat. No. 5,494,588, which is a continuation-in-part of Ser. No. 102,286, Aug. 5, 1993, abandoned.

[51] Int. Cl.$^6$ .................................................. C02F 1/50
[52] U.S. Cl. .................... 210/754; 210/755; 210/759; 210/764; 210/928; 252/175; 252/180; 422/28; 422/37; 514/557
[58] Field of Search .................................. 210/764, 928, 210/759, 754, 755; 252/175, 180; 422/28, 37; 514/557

[56] References Cited

U.S. PATENT DOCUMENTS

| | | | |
|---|---|---|---|
| 4,966,775 | 10/1990 | Donofrio et al. | 210/764 |
| 5,368,749 | 11/1994 | LaZonby | 210/756 |
| 5,395,530 | 3/1995 | Robertson et al. | 210/764 |
| 5,494,588 | 2/1996 | LaZonby | 210/755 |

*Primary Examiner*—Neil McCarthy
*Attorney, Agent, or Firm*—James J. Drake; Robert A. Miller

[57] ABSTRACT

The present invention provides a composition and method of administering same for inhibiting the growth of microorganisms. The composition of the present invention includes sufficient amounts of a peracetic acid and a non-oxidizing biocide. The method of the present invention includes the step of adding sufficient amounts of the peracetic acid and the non-oxidizing biocide to industrial process waters.

9 Claims, No Drawings

METHOD AND COMPOSITION FOR INHIBITING GROWTH OF MICROORGANISMS INCLUDING PERACETIC ACID AND A NON-OXIDIZING BIOCIDE

BACKGROUND OF THE INVENTION

1. Reference to Related Patent

The present application is a continuation-in-part of application Ser. No.08/350,570, filed Dec. 7, 1994, by Judy G. LaZonby, entitled "Method and Composition For Inhibiting Growth of Microorganisms Including Peracetic Acid and a Non-Oxidizing Biocide", now U.S. Pat. No. 5,494,588, which is in turn a continuation-in-part of application Ser. No. 08/102,286, filed Aug. 5, 1993, by Judy G. LaZonby, entitled "Method and Composition for Inhibiting Growth of Microorganisms Including Peracetic Acid and a Non-Oxidizing Biocide", now abandoned, the disclosures of which are incorporated herein by reference.

2. Field of the Invention

The present invention relates generally to controlling the growth of microorganisms. More specifically, the present invention relates to inhibiting the growth of microorganisms in industrial waters.

3. Background of the Invention

The presence of microorganisms in waters, especially industrial waters, is a never-ending concern for industrial manufacturers. Examples of industrial waters where microorganisms can interfere with industrial processes include: cooling tower waters; mining process waters; food processing waters; sugar reprocessing waters; and the like.

In the paper industry, the growth of microorganisms in pulp and paper mill waters can adversely affect finished paper products. Microbial life depends on nutrients, pH and temperature of a particular system. The warm temperatures and rich carbohydrate containing fluids of paper machines and process streams provide ideal growth conditions for a variety of microorganisms. These contaminating microorganisms are capable of causing spoilage of pulp, furnish, or chemical additives. The microorganisms cause deposits that break loose and fall into the paper furnish, resulting in quality loss and/or end product defects such as holes and spots. The end result is unstable paper or paper sold at a lower value. Robertson, *The use of phase-contrast microscopy to assess and differentiate the microbial population of a paper mill*, TAPPI Journal, pp. 83 (March 1993).

The presence of microorganisms within industrial water systems results in the formation of deposits of biological origin on industrial machines. These deposits give rise to: corrosion; breaks; increased down time; loss of yield; high chemical costs; odors; and expensive deposit control programs. In the paper mill industry, slime deposit are reportedly responsible for nearly 70% of all breaks, blockages and pump failures. Safade, *Tackling the Slime Problem in a Paper Mill*, PTI, p. 280 (September 1988).

Slime may be defined as an "accretion or accumulation caused by certain microorganisms in the presence of pulp fiber, filler, dirt and other materials, mixed in varied proportions, having variable physical characteristics and accumulating at continuously changing rates." Id. In most industrial process waters, especially pulp and paper mill systems, spore forming bacteria and *Pseudomonas arugiosa* contribute to slime formation. The later is most prevalent in paper mill slimes. Fungi is also a contributor of slime formation.

The conventional method of controlling microbial growth is through the use of biocides. Biocides are generally divided into two main groups: oxidizing; and non-oxidizing. These biocides act on the microorganisms in one of three ways: either by attacking the cell wall; the cytoplasmic membrane; or the cellular constituents. Id. at 282.

While biocides do inhibit microbial growth, economic and environmental concerns require improved methods. A problem with the use of biocides is that high levels of expensive chemicals are needed to control microbial growth. To date, none of the commercially available biocides have exhibited a prolonged biocidal effect. Their effectiveness is rapidly reduced as a result of exposure to physical conditions such as temperature or association with ingredients contained by the system toward which they exhibit an affinity. This results in a restriction or elimination of their biocidal effectiveness.

Therefore, the use of such biocides involves continuous or frequent additions to paper mill systems. Further, these additions must be made at a plurality of points or zones in the system. The costs of the biocides and the labor costs involved are considerable.

Moreover, such chemicals are highly toxic in the quantities known to be required for effective control of microbial populations. As a result, environmental regulations restrict the amount of biocides that can safely be discarded into the environment.

Therefore, a need exists for improved methods for controlling the growth of microorganisms in industrial process waters.

SUMMARY OF THE INVENTION

Pursuant to the present invention, the growth of microorganisms can be inhibited without the use of high levels of certain biocides. The present invention provides compositions to be used for controlling the growth of microorganisms in industrial process waters. The compositions include sufficient amounts of a peracetic acid and a non-oxidizing biocide. The composition of the present invention possesses unexpected synergistic activity against microorganisms, including bacteria and fungi. Peracetic acid is an organic biocide previously only used in the U.S. in the food industry at high concentrations. (0.1–1% product).

The present invention also provides a method for inhibiting the growth of the microorganisms in industrial process waters. Preferably, these process waters may be selected from the group consisting of pulp and paper mill process waters, industrial cooling waters and mining waters. The method includes the step of adding to the waters sufficient amounts of a peracetic acid (PAA) and a non-oxidizing biocide. Combining the peracetic acid with the non-oxidizing biocide has been found to enhance the effectiveness of the non-oxidizing biocide.

In an embodiment, the biocide is chosen from the group consisting of: isothiazolin; glutaraldehyde; DBNPA; methylene bisthlocyanate; carbamate; quaternary ammonium compounds; 4,5-dichloro-1,2-dithio-3-one; and 4,5-dichloro-2-N-octyl-4-isothiazolin-3-one, decylthioethylamine, orthophthaldehyde, 2-bromo-2-nitropropane-1,3-diol, 4,5-dichloro-1,2-dithiol-3-one, dodecylguanidine hydrochloride, 1-(3-chloroallyl)-3,5,7-triaza-1azoniaadamantane chloride, dibromo dicyanobutane and bis(trichloromethyl)sulfone.

In an embodiment, the peracetic acid is added prior to the biocide in the water system. An advantage of the present invention is that it provides improved compositions for use in inhibiting the growth of microorganisms. Another advantage of the present invention is that it provides an improved method for inhibiting the growth of microorganisms.

Still further, an advantage of the present invention is that it lowers the level of expensive chemicals needed for inhibiting the growth of microorganisms. With the addition of a peracetic acid in the water system, the non-oxidizing biocide is effective in low dosages, and as a result is long lasting as evidenced by reductions in microbial grow back. The increased effectiveness removes the need for repetitive additions of the biocide at multiple points in the paper making system.

Moreover, an advantage of the present invention is that it provides a more cost effective and environmentally friendly method for treating microorganisms.

Additional features and advantages of the present invention are described in, and will be apparent from, the detailed description of the presently preferred embodiments.

DETAILED DESCRIPTION OF THE PREFERRED EMBODIMENTS

The present invention provides, for inhibiting the growth of microorganisms, improved compositions and method of administering the same to a fluid system. The compositions include a sufficient amount of a peracetic acid and a non-oxidizing biocide.

The biocide component of this invention includes biocides that exhibit a synergistic effect when added to a fluid stream with a peracetic acid. Examples of suitable non-oxidizing biocides include: isothiazolin; methylene bisthiocyanate; glutaraldehyde; DBNPA; carbamate; quaternary ammonium compounds; 4,5-dichloro 1,2-dithio-3-one; and 4,5-dichloro-2-N-octyl-4-isothiazolin-3-one, decylthioethylamine, orthophthaldehyde, 2-bromo-2-nitropropane-1,3-diol, 4,5-dichloro-1,2-dithiol-3-one, dodecylguanidine hydrochloride, 1-(3-chloroallyl)-3,5,7-triaza-1-azoniaadamantane chloride, dibromo dicyanobutane and bis(trichloromethyl)sulfone. Naturally, mixtures of such biocides can also be used.

The biocides can be obtained from a number of chemical suppliers such as American Cyanamid, Buckman, Betz, Dearborn Chemical, Economics Laboratory, Inc., Merck, Nalco Chemical Company, and Vineland Chemical.

Peracetic acid may also be obtained from a number of chemical suppliers. One such supplier is FMC Corporation of Philadelphia, Pa.

The combination of a peracetic acid along with such non-oxidizing biocides provides an unexpected synergistic relationship. The synergistic relationship is present in that the cooperative action of the combined peracetic acid with the non-oxidizing biocides yields a total effect which is greater than the sum of the effects of the biocide or the peracetic acid taken separately.

The optimal amounts of biocide and peracetic acid required for effectiveness in this invention depend on the type of industrial waters being treated. In addition, the concentration of the combined components varies greatly and can depend upon the conditions such as temperature and pH of the waters, and the microbial count. The concentrations may be as little as 1 part per million (ppm) by weight to as much as 250 ppm. With respect to the biocide, the lower and upper limits of the required concentration substantially depend upon the specific biocide or combination of biocides used.

Still further, since the suitable biocides that may be used in the present invention are often obtained at different usable concentrations (i.e. activity level), the ratios vary depending on the particular biocide combined with the peracetic acid. For example, the peracetic acid used in the examples below is 5% active, the glutaraldehyde is 50% active, and the DBNPA is 20% active. Thus, a 1:1 ratio of PAA:Glut translates to 1:10 on an actives basis, while a 1:1 ratio of PAA:DBNPA translates to a 1:4 based on actives.

By way of example, and not limitation, the following are biocides, including the percent active of each biocide, that may be used in the present invention: isothiazolin (1.5% a.i.); glutaraldehyde (50% a.i.); methylene bisthiocyanate (10% a.i.); DBNPA (20% a.i.); carbamate (30% a.i.); quaternary ammonium compounds (31% a.i.); 4,5-dichloro-1,2-dithio-3-one (5% a.i.); and 4,5-dichloro-2-N-octyl-4-isothiazolin-3-one (2% a.i.), wherein "a.i." represents active ingredient.

Pursuant to the method of the present invention, the growth of microorganisms in industrial process waters can be inhibited. The method comprises the step of adding to the waters the peracetic acid and the nonoxidizing biocide of the present invention. In an embodiment, the biocide and the peracetic acid are separate components that are added to the system.

In a preferred embodiment, the peracetic acid is added to the industrial water prior to the addition of the non-oxidizing biocide. The peracetic acid can be added pursuant to any known method that provides the desired concentration of the same in the waters.

After the controlled addition of the peracetic acid, the non-oxidizing biocide is then added to the water system. In an embodiment, the non-oxidizing biocide is added 30 minutes after the peracetic acid is added to the system. Similar to the peracetic acid addition, the biocide can be added pursuant to any known method that provides the desired concentration of the biocide in the waters.

In an embodiment, the method comprises adding approximately 5 to 250 ppm of the non-oxidizing biocide along with approximately 10 to 250 ppm of the peracetic acid. In an embodiment, the biocide and the peracetic acid are present in a range from about 1 ppm to 1000 ppm of product.

Peracetic acid is a unique oxidant, utilizing a different mode of action than other oxidants. Given the structure of the molecule:

the hydrocarbon tail allows PAA to penetrate into the bacterial cell. This enables the molecule to disrupt S—S and S—H bonds both inside and outside of the organisms, killing more quickly and effectively than other oxidants. Other oxidants, such as HOCl, $ClO_2$, $H_2O_2$, etc. do not penetrate the cells in this manner because they do not have an organic portion to facilitate entrance into the bacterial cell.

Peracetic acid has always been applied by itself in high concentrations. Because it is also an equilibrium molecule, in that it dissociates back to its starting product after it is diluted, it was never expected to be active at low concentrations. However, its dissociation rate is much slower than expected, giving an unexpected synergy with other biocides when it is applied at low concentrations (as low as 10 ppm of a 5% product or 0.5 ppm active).

Peracetic acid has been used as a sterilant in the food industry for many years, but is generally used at higher concentrations (10,000 to 100,000 ppm). Until recently it has not been used in the paper industry for the control of microorganisms in the papermachine process water.

By way of example, and not limitation, examples of the invention will now be given.

EXAMPLES

The following examples illustrate the synergistic relationship obtained with the compositions of the present invention.

Synergy is mathematically demonstrated by the industry accepted method described by S. C. Kull et al. in *Allied Microbiology*, vol. 9, pages 538–541 (1961). As applied to this invention, it is as follows:

$Q_A$=the ppm of active non-oxidizing biocide alone which produces an endpoint.

$Q_B$=the ppm of active peracetic acid alone which produces an endpoint.

$Q_a$=the ppm of active peracetic acid, in combination with non-oxidizing biocide, which produces an endpoint.

$Q_b$=the ppm of active non-oxidizing biocide, in combination, which produces an endpoint.

$$\frac{Q_a}{Q_A} + \frac{Q_b}{Q_B} = \text{Synergy Index}$$
$$Q_A Q_B$$

<1, it indicates synergy
    =1, it indicates additivity
    >1, it indicates antagonism The following test procedures were utilized during the experimentation of the present invention.

Process water from several paper mills was obtained for test purposes. Aliquots of water from each mill were dosed with the indicated concentrations of peracetic acid (5% active obtained from FMC). After 30 minutes of contact time, the designated concentrations of non-oxidizing biocide were added to the aliquots previously dosed with PAA, mixed well and incubated at 37° C. in and orbital shaker. At the designated contact times, each aliquot was sampled to determine the total number of viable organisms in colony forming units per milliliter (CFU/mL) on Tryptone Glucose Extract (TGE) agar. An endpoint of 2,3,4 or 5 $\log_{10}$ reduction in viable organisms was then selected for calculating synergy.

Example 1

Synergistic activity against microorganisms was demonstrated in mill furnish at pH 7.0.

| Biocide (ppm product) | 30 Min. | 90 Min. | 5 Hours | 24 Hours |
|---|---|---|---|---|
| PAA-10 | $2.3 \times 10^6$ | $4.0 \times 10^6$ | $2.8 \times 10^6$ | $6.4 \times 10^6$ |
| PAA-20 | $5.8 \times 10^5$ | $9.3 \times 10^5$ | $2.3 \times 10^5$ | $6.5 \times 10^5$ |

| | 0 min. | 60 min. | 4.5 hr. | 24 hr. |
|---|---|---|---|---|
| Glut-50 | $3.2 \times 10^6$ | $3.2 \times 10^4$ | $<10^1$ | $<10^1$ |
| Glut-30 | $3.7 \times 10^6$ | $2.5 \times 10^5$ | $<10^1$ | $<10^1$ |
| Glut-20 | $4.2 \times 10^6$ | $7.2 \times 10^5$ | $2.6 \times 10^4$ | $1.1 \times 10^2$ |
| Glut-10 | $4.4 \times 10^6$ | $2.8 \times 10^6$ | $2.3 \times 10^6$ | $9.5 \times 10^2$ |
| Glut-10/PAA-10 | $4.5 \times 10^6$ | $3.2 \times 10^5$ | $5.3 \times 10^4$ | $1.9 \times 10^2$ |
| Glut-10/PAA-20 | $1.2 \times 10^5$ | $5.3 \times 10^4$ | $2.1 \times 10^4$ | $3.1 \times 10^2$ |
| Control-0 | $2.3 \times 10^6$ | $1.0 \times 10^5$ | $3.3 \times 10^6$ | $5.0 \times 10^6$ |

After 90 minutes of contact, a 2 $\log_{10}$ drop is achieved with:
PAA>20 ppm (40 ppm)
Glutaraldehyde=50 ppm
PAA=20 ppm/Glut=10 ppm
SI=10/50+20/40=0.7
After 5 hours of contact, a 2 $\log_{10}$ drop is achieved with:
PAA>20 ppm (40 ppm)
Glutaraldehyde=20 ppm
PAA=10 ppm/glut=10 ppm
SI=10/40+10/20=0.75
After 24 hours of contact, a 4 $\log_{10}$ drop is achieved with:
PAA>20 ppm (40 ppm)
Glutaraldehyde=20 ppm
PAA=10 ppm/glut=10 ppm
SI=10/40+10/20=0.75

Example 2

| Biocide (ppm product) | 30 Min. | 90 Min. | 5 Hours | 24 Hours |
|---|---|---|---|---|
| PAA-5 | $7.4 \times 10^5$ | $8.5 \times 10^5$ | $7.8 \times 10^5$ | $8.8 \times 10^6$ |
| PAA-10 | $6.4 \times 10^5$ | $6.7 \times 10^5$ | $5.2 \times 10^5$ | $2.9 \times 10^6$ |
| PAA-20 | $4.0 \times 10^5$ | $5.4 \times 10^5$ | $1.0 \times 10^5$ | $5.1 \times 10^5$ |

| | 0 min. | 60 min. | 4.5 hr. | 24 hr. |
|---|---|---|---|---|
| DBNPA-100 | $3.9 \times 10^5$ | $<10^1$ | $<10^1$ | $<10^1$ |
| DBNPA-75 | $5.1 \times 10^5$ | $<10^1$ | $<10^1$ | $<10^1$ |
| DBNPA-50 | $6.0 \times 10^5$ | $8.1 \times 10^2$ | $<10^1$ | $<10^1$ |
| DBNPA-25 | $6.0 \times 10^5$ | $3.3 \times 10^3$ | $<10^1$ | $9.4 \times 10^4$ |
| DBNPA-100/PAA-5 | $4.3 \times 10^5$ | $<10^1$ | $<10^1$ | $<10^1$ |
| DBNPA-75/PAA-5 | $6.1 \times 10^5$ | $<10^1$ | $<10^1$ | $<10^1$ |
| DBNPA-50/PAA-5 | $3.7 \times 10^5$ | $<10^1$ | $<10^1$ | $<10^1$ |
| DBNPA-25/PAA-5 | $8.8 \times 10^5$ | $3.4 \times 10^3$ | $1.1 \times 10^2$ | $<10^1$ |
| DBNPA-100/PAA-10 | $5.5 \times 10^5$ | $<10^1$ | $<10^1$ | $<10^1$ |
| DBNPA-75/PAA-10 | $1.4 \times 10^5$ | $<10^1$ | $<10^1$ | $<10^1$ |
| DBNPA-50/PAA-10 | $9.5 \times 10^4$ | $<10^1$ | $<10^1$ | $<10^1$ |
| DBNPA-25/PAA-10 | $3.6 \times 10^4$ | $<10^1$ | $<10^1$ | $<10^1$ |
| DBNPA-100/PAA-20 | $2.0 \times 10^5$ | $<10^1$ | $<10^1$ | $<10^1$ |
| DBNPA-75/PAA-20 | $5.4 \times 10^5$ | $<10^1$ | $<10^1$ | $<10^1$ |
| DBNPA-50/PAA-20 | $4.5 \times 10^5$ | $<10^1$ | $<10^1$ | $<10^1$ |
| DBNPA-25/PAA-20 | $3.7 \times 10^5$ | $<10^1$ | $<10^1$ | $<10^1$ |
| Control-0 | $3.7 \times 10^5$ | $9.0 \times 10^5$ | $3.0 \times 10^5$ | $2.4 \times 10^6$ |

After 90 minutes of contact, a 5 $\log_{10}$ drop is achieved with:
PAA>20 ppm (40 ppm)
DBNPA=75 ppm
PAA=5 ppm/DBNPA=50 ppm
SI=5/40+50/75=0.79
PAA=10 ppm/DBNPA=25 ppm
SI=10/40+25/75=0.58
After 24 hours of contact, a 5 $\log_{10}$ drop is achieved with:
PAA>20 ppm (40 ppm)
DBNPA=50 ppm
PAA=5 ppm/DBNPA=25 ppm
SI=5/40+25/50=0.625

Example 3

Synergistic activity against microorganisms was demonstrated in mill furnish at pH 7.1.

| Biocide (ppm product) | 30 Min. | 2 Hours | 5 Hours | 24 Hours |
|---|---|---|---|---|
| PAA-25 | $2.2 \times 10^6$ | $1.4 \times 10^6$ | $2.9 \times 10^6$ | $7.3 \times 10^6$ |
| PAA-50 | $2.9 \times 10^4$ | $7.5 \times 10^4$ | $2.1 \times 10^4$ | $1.8 \times 10^6$ |
| PAA-100 | $6.8 \times 10^2$ | $6.1 \times 10^2$ | $5.9 \times 10^2$ | $2.4 \times 10^6$ |

-continued

| Biocide (ppm product) | 0 Min. | 1.5 Hrs. | 4.5 Hrs. | 24 Hrs. |
|---|---|---|---|---|
| MBT-5 | | $9.8 \times 10^6$ | $7.1 \times 10^6$ | $1.6 \times 10^6$ |
| MBT-10 | | $3.6 \times 10^6$ | $5.7 \times 10^6$ | $3.8 \times 10^6$ |
| MBT-25 | | $2.4 \times 10^6$ | $8.0 \times 10^5$ | $7.5 \times 10^6$ |
| MBT-50 | $2.2 \times 10^6$ | $2.1 \times 10^6$ | $2.1 \times 10^5$ | $3.4 \times 10^5$ |
| PAA-10/MBT-5 | | $3.8 \times 10^6$ | $7.7 \times 10^6$ | $4.6 \times 10^7$ |
| PAA-10/MBT-10 | | $4.3 \times 10^6$ | $5.2 \times 10^6$ | $4.5 \times 10^7$ |
| PAA-10/MBT-25 | | $1.9 \times 10^6$ | $2.6 \times 10^6$ | $1.1 \times 10^7$ |
| PAA-10/MBT-50 | $3.8 \times 10^6$ | $1.7 \times 10^6$ | $3.4 \times 10^5$ | $7.7 \times 10^4$ |
| PAA-20/MBT-5 | | $1.4 \times 10^6$ | $2.1 \times 10^6$ | $1.8 \times 10^7$ |
| PAA-20/MBT-10 | | $1.9 \times 10^6$ | $1.1 \times 10^6$ | $1.6 \times 10^7$ |
| PAA-20/MBT-25 | | $1.1 \times 10^5$ | $4.6 \times 10^5$ | $3.3 \times 10^6$ |
| PAA-20/MBT-50 | $1.7 \times 10^6$ | $6.0 \times 10^5$ | $6.3 \times 10^4$ | $2.4 \times 10^3$ |
| PAA-40/MBT-5 | | $8.2 \times 10^4$ | $2.8 \times 10^4$ | $1.2 \times 10^7$ |
| PAA-40/MBT-10 | | $9.2 \times 10^4$ | $2.5 \times 10^4$ | $1.3 \times 10^7$ |
| PAA-40/MBT-25 | | $6.3 \times 10^4$ | $1.6 \times 10^4$ | $4.0 \times 10^5$ |
| PAA-40/MBT-50 | $1.4 \times 10^5$ | $4.9 \times 10^4$ | $2.2 \times 10^4$ | $1.8 \times 10^3$ |
| Control-0 | $1.1 \times 10^7$ | $1.5 \times 10^7$ | $3.1 \times 10^7$ | $7.5 \times 10^3$ |

After 24 hours of contact, a 3 $\log_{10}$ drop is achieved with:
PAA>100 ppm (200 ppm)
MBT>50 ppm (100 ppm)
PAA=20 ppm/MBT=50 ppm
SI=20/200+50/100=0.6
After 5 hours of contact, a 3 $\log_{10}$ drop is achieved with:
PAA>50 ppm
MBT>50 ppm (100 ppm)
PAA=20 ppm/MBT=50 ppm
SI=20/50+50/100=0.9

Example 4

Synergistic activity against microorganisms was demonstrated in mill furnish at pH 7.28.

| Biocide (ppm product) | 30 Min. | 2 Hours | 5 Hours | 24 Hours |
|---|---|---|---|---|
| PAA-25 | $1.3 \times 10^5$ | $2.4 \times 10^5$ | $1.8 \times 10^6$ | $3.0 \times 10^7$ |
| PAA-50 | $1.6 \times 10^3$ | $2.5 \times 10^3$ | $1.0 \times 10^4$ | $1.7 \times 10^7$ |
| PAA-100 | $1.3 \times 10^2$ | $1.5 \times 10^3$ | $1.5 \times 10^3$ | $8.1 \times 10^6$ |

| | 0 Min. | 1.5 Hr. | 4.5 Hr. | 24 Hr. |
|---|---|---|---|---|
| CARB-50 | | $9.8 \times 10^6$ | $1.1 \times 10^7$ | $2.6 \times 10^6$ |
| CARB-100 | | $9.4 \times 10^6$ | $7.2 \times 10^6$ | $7.8 \times 10^4$ |
| CARB-150 | | $1.1 \times 10^6$ | $1.0 \times 10^6$ | $3.8 \times 10^4$ |
| CARB-200 | $4.7 \times 10^6$ | $1.8 \times 10^6$ | $1.0 \times 10^6$ | $3.0 \times 10^4$ |
| PAA-10/CARB-50 | | $2.8 \times 10^6$ | $2.5 \times 10^6$ | $2.8 \times 10^4$ |
| PAA-10/CARB-100 | | $3.2 \times 10^6$ | $5.0 \times 10^4$ | $4.0 \times 10^4$ |
| PAA-10/CARB-150 | | $3.0 \times 10^6$ | $2.6 \times 10^4$ | $4.8 \times 10^4$ |
| PAA-10/CARB-200 | $2.2 \times 10^6$ | $1.4 \times 10^5$ | $5.9 \times 10^4$ | $2.5 \times 10^3$ |
| PAA-20/CARB-50 | | $1.1 \times 10^5$ | $2.0 \times 10^6$ | $2.1 \times 10^3$ |
| PAA-20/CARB-100 | | $3.9 \times 10^4$ | $4.5 \times 10^4$ | $1.2 \times 10^3$ |
| PAA-20/CARB-150 | | $2.3 \times 10^4$ | $2.5 \times 10^4$ | $1.5 \times 10^3$ |
| PAA-20/CARB-200 | $3.7 \times 10^5$ | $2.5 \times 10^4$ | $1.9 \times 10^4$ | $8.1 \times 10^2$ |
| PAA-40/CARB-50 | | $2.3 \times 10^3$ | $1.2 \times 10^3$ | $9.3 \times 10^2$ |
| PAA-40/CARB-100 | | $2.0 \times 10^3$ | $7.0 \times 10^2$ | $5.4 \times 10^2$ |
| PAA-40/CARB-150 | | $1.4 \times 10^3$ | $6.6 \times 10^2$ | $6.8 \times 10^2$ |
| PAA-40/CARB-200 | $1.0 \times 10^4$ | $1.3 \times 10^3$ | $5.6 \times 10^2$ | $6.0 \times 10^2$ |
| Control-0 | $1.2 \times 10^7$ | $3.0 \times 10^6$ | $3.0 \times 10^6$ | $3.2 \times 10^7$ |

After 2 hours of contact, a 2 $\log_{10}$ drop was achieved with:
PAA=50 ppm
CARB>200 ppm (400 ppm)
PAA=20 ppm/CARB=100 ppm
SI=20/50+100/400=0.65
PAA=40 ppm/CARB<50 ppm
SI=40/50+25/400=0.8625
After 5 hours of contact, a 4 $\log_{10}$ drop was achieved with:
PAA>100 ppm (200 ppm)
CARB>200 ppm (400 ppm)
PAA=40 ppm/CARB=100 ppm
SI=40/200+100/400=0.45
After 24 hours of contact, a 4 $\log_{10}$ drop was achieved with:
PAA>100 ppm (200 ppm)
CARB>200 ppm (400 ppm)
PAA=10 ppm/CARB=200 ppm
SI=10/200+200/400=0.55
PAA=20 ppm/CARB=50 ppm
SI=20/200+50/400=0.225
PAA=40 ppm/CARB=50 ppm
SI=40/200+50/400=0.325

Example 5

| Biocide (ppm product) | 30 Min. | 3 Hours | 5 Hours | 24 Hours |
|---|---|---|---|---|
| PAA-25 | $4.2 \times 10^6$ | $5.4 \times 10^6$ | $5.3 \times 10^6$ | $1.7 \times 10^7$ |
| PAA-50 | $4.4 \times 10^4$ | $1.1 \times 10^5$ | $7.3 \times 10^4$ | $1.9 \times 10^7$ |
| PAA-100 | $8.0 \times 10^2$ | $1.1 \times 10^3$ | $1.1 \times 10^3$ | $1.3 \times 10^7$ |

| | 0 Min. | 2.5 Hr. | 4.5 Hr. | 24 Hr. |
|---|---|---|---|---|
| QUAT-25 | | $2.7 \times 10^5$ | $3.0 \times 10^5$ | $1.8 \times 10^7$ |
| QUAT-50 | | $1.0 \times 10^5$ | $1.7 \times 10^5$ | $1.1 \times 10^7$ |
| QUAT-100 | | $7.9 \times 10^4$ | $8.6 \times 10^4$ | $5.2 \times 10^6$ |
| QUAT-200 | $7.5 \times 10^4$ | $6.4 \times 10^2$ | $7.2 \times 10^2$ | $1.6 \times 10^2$ |
| PAA-10/QUAT-25 | | $1.2 \times 10^5$ | $2.0 \times 10^5$ | $1.7 \times 10^7$ |
| PAA-10/QUAT-50 | | $6.6 \times 10^4$ | $1.3 \times 10^5$ | $7.3 \times 10^6$ |
| PAA-10/QUAT-100 | | $1.3 \times 10^3$ | $3.1 \times 10^3$ | $1.6 \times 10^7$ |
| PAA-10/QUAT-200 | $1.7 \times 10^5$ | $5.0 \times 10^2$ | $6.8 \times 10^2$ | $2.9 \times 10^6$ |
| PAA-20/QUAT-25 | | $1.8 \times 10^5$ | $1.2 \times 10^5$ | $4.9 \times 10^6$ |
| PAA-20/QUAT-50 | | $9.1 \times 10^4$ | $1.2 \times 10^5$ | $6.5 \times 10^6$ |
| PAA-20/QUAT-100 | | $3.9 \times 10^3$ | $6.8 \times 10^3$ | $5.0 \times 10^6$ |
| PAA-20/QUAT-200 | $6.3 \times 10^4$ | $5.4 \times 10^2$ | $6.6 \times 10^2$ | $2.4 \times 10^2$ |
| PAA-40/QUAT-25 | | $3.4 \times 10^3$ | $4.0 \times 10^3$ | $8.9 \times 10^6$ |
| PAA-40/QUAT-50 | | $1.9 \times 10^3$ | $1.7 \times 10^3$ | $3.0 \times 10^5$ |
| PAA-40/QUAT-100 | | $2.0 \times 10^3$ | $1.7 \times 10^3$ | $4.0 \times 10^5$ |
| PAA-40/QUAT-200 | $1.3 \times 10^3$ | $3.7 \times 10^2$ | $5.3 \times 10^2$ | $1.9 \times 10^2$ |
| Control-0 | $1.1 \times 10^7$ | $1.4 \times 10^7$ | $1.3 \times 10^7$ | $2.1 \times 10^7$ |

After 24 hours of contact, a 2 $\log_{10}$ drop was achieved with:
PAA>100 ppm (200 ppm)
QUAT=200 ppm
PAA=40 ppm/QUAT=50 ppm
SI=40/200+50/200=0.45
After 3 hours & 5 hours of contact, a 4 $\log_{10}$ drop was achieved with:
PAA=100 ppm
QUAT=200 ppm
PAA=40 ppm/QUAT=25 ppm
SI=40/100+25/200=0.525

Example 6

Synergistic activity against microorganisms was demonstrated in mill furnish at pH 7.5.

| Biocide (ppm product) | 30 Min. | 90 Min. | 5 Hours | 24 Hours |
|---|---|---|---|---|
| PAA-10 | $4.9 \times 10^5$ | $5.0 \times 10^5$ | $2.5 \times 10^6$ | $9.6 \times 10^6$ |
| PAA-25 | $2.9 \times 10^5$ | $4.8 \times 10^5$ | $4.2 \times 10^6$ | $2.3 \times 10^6$ |
| PAA-50 | $6.3 \times 10^4$ | $1.8 \times 10^5$ | $4.1 \times 10^5$ | $2.5 \times 10^7$ |

| | 0 Min. | 60 Min. | 4.5 Hr. | 24 Hr. |
|---|---|---|---|---|
| ISO-133 | $7.4 \times 10^5$ | $5.1 \times 10^5$ | $4.7 \times 10^5$ | $1.6 \times 10^4$ |
| ISO-100 | $7.3 \times 10^5$ | $5.6 \times 10^5$ | $4.2 \times 10^5$ | $1.9 \times 10^4$ |
| ISO-67 | $7.8 \times 10^5$ | $5.9 \times 10^5$ | $3.8 \times 10^5$ | $9.6 \times 10^4$ |
| ISO-33 | $8.0 \times 10^5$ | $5.7 \times 10^5$ | $6.1 \times 10^5$ | $2.2 \times 10^7$ |
| PAA-10/ISO-133 | $5.2 \times 10^5$ | $1.6 \times 10^5$ | $2.1 \times 10^5$ | $1.1 \times 10^4$ |
| PAA-10/ISO-100 | $3.1 \times 10^5$ | $1.4 \times 10^5$ | $3.4 \times 10^5$ | $2.1 \times 10^4$ |
| PAA-10/ISO-67 | $3.7 \times 10^5$ | $2.1 \times 10^5$ | $4.8 \times 10^5$ | $4.9 \times 10^4$ |
| PAA-10/ISO-33 | $2.6 \times 10^5$ | $2.2 \times 10^5$ | $6.4 \times 10^5$ | $5.3 \times 10^6$ |
| PAA-25/ISO-133 | $1.4 \times 10^5$ | $6.7 \times 10^4$ | $1.1 \times 10^5$ | $3.2 \times 10^3$ |
| PAA-25/ISO-100 | $1.6 \times 10^5$ | $8.7 \times 10^4$ | $1.2 \times 10^5$ | $4.2 \times 10^3$ |
| PAA-25/ISO-67 | $1.2 \times 10^{5+}$ | $8.0 \times 10^4$ | $1.4 \times 10^5$ | $4.9 \times 10^3$ |
| PAA-25/ISO-133 | $1.5 \times 10^5$ | $9.4 \times 10^4$ | $1.6 \times 10^5$ | $9.8 \times 10^3$ |
| PAA-50/ISO-133 | $1.8 \times 10^4$ | $5.5 \times 10^3$ | $5.3 \times 10^3$ | $1.6 \times 10^2$ |
| PAA-50/ISO-100 | $1.4 \times 10^4$ | $6.8 \times 10^3$ | $3.5 \times 10^4$ | $3.2 \times 10^2$ |
| PAA-50/ISO-67 | $3.3 \times 10^4$ | $1.2 \times 10^4$ | $3.3 \times 10^4$ | $1.1 \times 10^3$ |
| PAA-50/ISO-33 | $1.9 \times 10^4$ | $2.3 \times 10^4$ | $5.1 \times 10^4$ | $5.4 \times 10^3$ |
| Control-0 | $8.2 \times 10^5$ | $7.1 \times 10^5$ | $2.5 \times 10^6$ | $4.3 \times 10^6$ |

After 90 minutes of contact, a 1 $\log_{10}$ drop was achieved with:

PAA>50 ppm (100 ppm)
ISO>133 ppm (167 ppm)
PAA=25 ppm/ISO=67 ppm
SI=25/100+67/167=0.65

After 5 hours of contact, a 2 $\log_{10}$ drop was achieved with:

PAA>50 ppm (100 ppm)
ISO>133 ppm (167 ppm)
PAA>50 ppm/ISO=33 ppm
SI=50/100+33/167=0.70

After 24 hours of contact, a 3 $\log_{10}$ drop was achieved with:

PAA>50 ppm (100 ppm)
ISO>133 ppm (167 ppm)
PAA=25 ppm/ISO=67 ppm
SI=25/100+67/167=0.65

Example 7

Trials were conducted at a paper mill where inadequate antimicrobial control was being applied and slime began to develop on machine surfaces. The aerobic bacterial population on the machine surfaces was found to persist at $1 \times 10^7$ CFU/mL. At counts higher than this, the mill experiences sever slime problems and the quality of paper being produced is compromised.

If a 1.5% isothiazolin blend is fed to this machine as a sole biocide, 150 ppm of the 1.5% isothiazolin blend is needed to hold the population to $5 \times 10^6$ CFU/mL. However, over an extended period of time, even this high dosage becomes inadequate. A combination of 10 ppm of a 4.5% peracetic acid solution and 17 ppm of the 1.5% isothiazolin blend allowed the counts to increase to the level of $1 \times 10^7$ CFU/mL. By increasing the 1.5% isothiazolin blend to 33 ppm, the population dropped to $1 \times 10^4$ CFU/mL.

Laboratory testing has shown that a 50 ppm dose of the 4.5% peracetic acid solution is needed to drop the population to $10^4$ CFU/mL by itself. Using this information, a synergy index can be calculated:

To achieve a 3 log drop:
  alone 4.5% peracetic acid solution=50 ppm
  alone 1.5% isothiazolin blend>150 ppm (200 ppm) or
  Combination of 10 ppm 4.5% peracetic acid solution+ 33 ppm of N-7647 Synergy Index
  10/50+33/200=0.365

The 4.5% peracetic acid solution was being fed continuously to the whitewater loop and the 1.5% isothiazolin blend was being fed intermittently to the same application point. On an actives basis, when the 1.5% isothiazolin blend was being added, this ratio is very close to 1:1. This range will vary, mill to mill, anywhere from 5:1 to 1:5 for this combination. Based on the laboratory data, ratios for other biocide combinations would be expected to range from 1:1 to 1:200, on an actives basis.

The present invention lowers the levels of expensive chemicals needed for inhibiting the growth of microorganisms. As illustrated in the figure, a 100 ppm dosage of biocide, such as carbamate, in combination with 20 ppm dosage of peracetic acid is more effective than administering either 25 ppm of peracetic acid or 200 ppm of the biocide alone. Accordingly, the present invention provides a more cost effective and environmentally friendly method for treating microorganisms.

Example 8

In an attempt to demonstrate synergistic activity of peracetic acid and bromohydroxyacetophenone (BHAP) against microorganisms found in paper mill whitewater, pH 7.1, the following experiment was performed. However, instead of synergistic activity, it was found that these 2 biocides are antagonistic. Although this was not the intended result, this experiment shows that peracetic acid is not synergistic with all organic biocides.

| Biocide (ppm product) | 60 min | 300 min | 24 Hours |
|---|---|---|---|
| PAA-25 | $2.9 \times 10^6$ | $1.7 \times 10^7$ | $2.7 \times 10^7$ |
| PAA-50 | $1.5 \times 10^6$ | $4.7 \times 10^6$ | $4.0 \times 10^7$ |
| PAA-100 | $1.1 \times 10^6$ | $1.6 \times 10^5$ | $6.5 \times 10^7$ |

| | 30 min | 270 min | 24 Hours |
|---|---|---|---|
| BHAP-12.5 | $2.4 \times 10^6$ | $9.8 \times 10^4$ | $4.5 \times 10^7$ |
| BHAP-25 | $1.4 \times 10^6$ | $2.7 \times 10^4$ | $1.7 \times 10^7$ |
| BHAP-50 | $6.0 \times 10^5$ | $6.2 \times 10^4$ | $1.0 \times 10^3$ |
| BHAP-100 | $4.2 \times 10^5$ | $1.3 \times 10^4$ | $1.5 \times 10^2$ |
| PAA-10/BHAP-12.5 | $3.9 \times 10^6$ | $6.0 \times 10^5$ | $4.9 \times 10^7$ |
| PAA-10/BHAP-25 | $2.7 \times 10^6$ | $1.9 \times 10^5$ | $1.9 \times 10^7$ |
| PAA-10/BHAP-50 | $1.0 \times 10^6$ | $8.5 \times 10^4$ | $1.8 \times 10^7$ |
| PAA-10/BHAP-100 | $2.0 \times 10^6$ | $1.1 \times 10^5$ | $9.7 \times 10^2$ |
| PAA-20/BHAP-12.5 | $3.6 \times 10^6$ | $1.2 \times 10^6$ | $4.1 \times 10^7$ |
| PAA-20/BHAP-25 | $2.0 \times 10^6$ | $7.0 \times 10^5$ | $1.6 \times 10^7$ |
| PAA-20/BHAP-50 | $1.8 \times 10^6$ | $8.7 \times 10^4$ | $8.2 \times 10^4$ |
| PAA-20/BHAP-100 | $1.4 \times 10^6$ | $5.3 \times 10^4$ | $3.2 \times 10^2$ |
| PAA-40/BHAP-12.5 | $1.5 \times 10^6$ | $1.9 \times 10^6$ | $4.8 \times 10^7$ |
| PAA-40/BHAP-25 | $1.8 \times 10^6$ | $7.1 \times 10^4$ | $2.6 \times 10^7$ |
| PAA-40/BHAP-50 | $1.4 \times 10^6$ | $9.0 \times 10^4$ | $2.0 \times 10^5$ |
| PAA-40/BHAP-100 | $9.0 \times 10^5$ | $6.7 \times 10^4$ | $3.0 \times 10^2$ |
| Control - 0 | $7.1 \times 10^6$ | $6.0 \times 10^6$ | $1.0 \times 10^7$ |

Synergy Calculation:

For a 4 $\log_{10}$ reduction after 24 hours contact:

PAA=>100 (200)
BHAP=50
PAA/BHAP=10/100 10/200+100/50=2.05=SI

Example 9

Synergistic activity of peracetic acid and dibromo dicyanobutane (DBDCB) against microorganisms was demonstrated in paper mill process water at pH 7.0.

| Biocide (ppm product) | 60 min | 300 min | 24 Hours |
|---|---|---|---|
| PAA-25 | $3.3 \times 10^6$ | $1.1 \times 10^7$ | $1.3 \times 10^7$ |
| PAA-50 | $6.4 \times 10^5$ | $5.6 \times 10^6$ | $3.4 \times 10^7$ |
| PAA-100 | $2.7 \times 10^5$ | $1.6 \times 10^4$ | $3.0 \times 10^7$ |

| | 30 min | 270 min | 24 Hours |
|---|---|---|---|
| DBDCB-25 | $2.1 \times 10^6$ | $8.1 \times 10^4$ | $4.5 \times 10^6$ |
| DBDCB-50 | $2.2 \times 10^6$ | $1.1 \times 10^3$ | $1.8 \times 10^2$ |
| DBDCB-100 | $3.6 \times 10^6$ | $2.0 \times 10^3$ | $<10^1$ |
| DBDCB-200 | $2.8 \times 10^6$ | $9.7 \times 10^2$ | $<10^1$ |
| PAA-10/DBDCB-25 | $3.9 \times 10^6$ | $1.1 \times 10^5$ | $6.5 \times 10^2$ |
| PAA-10/DBDCB-50 | $3.1 \times 10^6$ | $8.2 \times 10^3$ | $4.3 \times 10^2$ |
| PAA-10/DBDCB-100 | $1.9 \times 10^6$ | $2.9 \times 10^3$ | $<10^1$ |
| PAA-10/DBDCB-200 | $3.7 \times 10^6$ | $3.7 \times 10^3$ | $<10^1$ |
| PAA-20/DBDCB-25 | $2.6 \times 10^6$ | $3.4 \times 10^5$ | $2.9 \times 10^3$ |
| PAA-20/DBDCB-50 | $2.1 \times 10^6$ | $1.3 \times 10^3$ | $2.1 \times 10^2$ |
| PAA-20/DBDCB-100 | $1.8 \times 10^6$ | $7.0 \times 10^3$ | $4.8 \times 10^1$ |
| PAA-20/DBDCB-200 | $3.7 \times 10^6$ | $3.7 \times 10^3$ | $2.1 \times 10^1$ |
| PAA-40/DBDCB-25 | $1.7 \times 10^6$ | $2.9 \times 10^4$ | $6.8 \times 10^2$ |
| PAA-40/DBDCB-50 | $1.7 \times 10^6$ | $9.1 \times 10^3$ | $4.1 \times 10^2$ |
| PAA-40/DBDCB-100 | $3.3 \times 10^5$ | $2.4 \times 10^3$ | $1.3 \times 10^1$ |
| PAA-40/DBDCB-200 | $2.4 \times 10^5$ | $2.3 \times 10^3$ | $<10^1$ |
| Control - 0 | $5.5 \times 10^6$ | $6.6 \times 10^6$ | $7.4 \times 10^6$ |

Synergy Calculation:

For a 4 $_{10}$log reduction after 24 hours contact:

PAA=>100 (200)

DBDCB=50

PAA/DBDCB=10/25 10/200+25/50=0.55=SI

Example 10

When attempting to demonstrate the synergistic activity of peracetic acid and dodecyl guanidine hydrochloride against bacteria found in paper mill whitewater at pH 7.1, it was discovered that synergy occurs with these chemicals after 1 hour of exposure, but their effects are antagonistic after 24 hours of static exposure. This experiment demonstrates the importance of feeding the chemicals at the correct intervals to ensure the desired result.

| Biocide (ppm product) | 60 min | 300 min | 24 Hours |
|---|---|---|---|
| PAA-25 | $3.8 \times 10^5$ | $4.6 \times 10^6$ | $4.3 \times 10^7$ |
| PAA-50 | $2.5 \times 10^5$ | $4.5 \times 10^6$ | $2.7 \times 10^7$ |
| PAA-100 | $1.9 \times 10^5$ | $2.0 \times 10^4$ | $2.1 \times 10^7$ |

| | 30 min | 270 min | 24 Hours |
|---|---|---|---|
| DGH-10 | $3.6 \times 10^5$ | $3.2 \times 10^6$ | $2.4 \times 10^7$ |
| DGH-20 | $3.3 \times 10^5$ | $4.3 \times 10^5$ | $3.0 \times 10^7$ |
| DGH-40 | $5.4 \times 10^4$ | $7.6 \times 10^2$ | $6.1 \times 10^4$ |
| DGH-80 | $2.7 \times 10^2$ | $<10^1$ | $2.8 \times 10^2$ |
| PAA-10/DGH-10 | $4.6 \times 10^5$ | $4.0 \times 10^6$ | $2.3 \times 10^7$ |
| PAA-10/DGH-20 | $1.7 \times 10^5$ | $1.2 \times 10^5$ | $1.9 \times 10^7$ |
| PAA-10/DGH-40 | $2.4 \times 10^3$ | $8.2 \times 10^2$ | $2.7 \times 10^4$ |
| PAA-10/DGH-80 | $2.5 \times 10^2$ | $<10^1$ | $4.6 \times 10^2$ |
| PAA-20/DGH-10 | $4.9 \times 10^5$ | $3.7 \times 10^6$ | $1.9 \times 10^7$ |
| PAA-20/DGH-20 | $3.4 \times 10^5$ | $3.2 \times 10^5$ | $1.8 \times 10^7$ |
| PAA-20/DGH-40 | $1.6 \times 10^3$ | $2.9 \times 10^3$ | $2.0 \times 10^7$ |
| PAA-20/DGH-80 | $3.5 \times 10^2$ | $2.8 \times 10^1$ | $2.3 \times 10^5$ |
| PAA-40/DGH-10 | $1.9 \times 10^5$ | $9.8 \times 10^5$ | $2.1 \times 10^7$ |
| PAA-40/DGH-20 | $3.2 \times 10^5$ | $1.2 \times 10^6$ | $1.6 \times 10^7$ |
| PAA-40/DGH-40 | $1.6 \times 10^2$ | $2.8 \times 10^2$ | $1.5 \times 10^7$ |
| PAA-40/DGH-80 | $1.6 \times 10^2$ | $1.9 \times 10^1$ | $2.0 \times 10^7$ |
| Control - 0 | $5.5 \times 10^6$ | $6.6 \times 10^6$ | $7.4 \times 10^6$ |

Synergy Calculation:

For a 3 $_{10}$log reduction after 1 hours contact:

PAA=>100 (200)

DGH=80

PAA/DGH=40/40 40/200+40/80=0.7=SI Synergy

For a 5 $\log_{10}$ reduction after 24 hours of contact:

PAA=>100 (200)

DGH=80

PAA/DGH=40(80)/>80(160) 80/200+160/80=2.4=SI Antagonism

Example 11

Synergistic activity of peracetic acid and dodecylthioethylamine (DTEA) against microorganisms was demonstrated in paper mill whitewater, pH 7.1.

| Biocide (ppm product) | 60 min | 300 min | 24 Hours |
|---|---|---|---|
| PAA-20 | $6.5 \times 10^5$ | $2.9 \times 10^6$ | $8.4 \times 10^6$ |
| PAA-40 | $8.7 \times 10^4$ | $7.0 \times 10^4$ | $3.1 \times 10^7$ |
| PAA-80 | $1.3 \times 10^4$ | $2.9 \times 10^3$ | $1.8 \times 10^7$ |

| | 30 min | 270 min | 24 Hours |
|---|---|---|---|
| DTEA-12.5 | $1.0 \times 10^7$ | $1.1 \times 10^7$ | $1.5 \times 10^7$ |
| DTEA-25 | $1.2 \times 10^7$ | $1.1 \times 10^7$ | $1.5 \times 10^7$ |
| DTEA-50 | $1.2 \times 10^7$ | $9.5 \times 10^6$ | $1.8 \times 10^7$ |
| DTEA-100 | $5.0 \times 10^6$ | $1.1 \times 10^6$ | $3.2 \times 10^7$ |
| PAA-10/DTEA-12.5 | $3.0 \times 10^6$ | $7.5 \times 10^6$ | $1.9 \times 10^7$ |
| PAA-10/DTEA-25 | $3.5 \times 10^6$ | $8.6 \times 10^6$ | $1.8 \times 10^7$ |
| PAA-10/DTEA-50 | $2.7 \times 10^6$ | $4.8 \times 10^6$ | $3.0 \times 10^7$ |
| PAA-10/DTEA-100 | $1.1 \times 10^2$ | $5.0 \times 10^5$ | $3.4 \times 10^7$ |
| PAA-20/DTEA-12.5 | $6.3 \times 10^5$ | $2.1 \times 10^6$ | $2.0 \times 10^7$ |
| PAA-20/DTEA-25 | $7.1 \times 10^5$ | $1.8 \times 10^6$ | $2.7 \times 10^7$ |
| PAA-20/DTEA-50 | $6.3 \times 10^5$ | $7.5 \times 10^5$ | $1.7 \times 10^7$ |
| PAA-20/DTEA-100 | $2.3 \times 10^5$ | $8.9 \times 10^4$ | $3.1 \times 10^7$ |
| PAA-40/DTEA-12.5 | $3.8 \times 10^3$ | $7.3 \times 10^3$ | $3.1 \times 10^7$ |
| PAA-40/DTEA-25 | $5.2 \times 10^3$ | $5.2 \times 10^2$ | $2.4 \times 10^7$ |
| PAA-40/DTEA-50 | $4.7 \times 10^3$ | $4.8 \times 10^3$ | $3.6 \times 10^7$ |
| PAA-40/DTEA-100 | $2.5 \times 10^3$ | $2.0 \times 10^3$ | $3.7 \times 10^7$ |
| Control - 0 | $1.6 \times 10^7$ | $1.8 \times 10^7$ | $1.2 \times 10^7$ |

Synergy Calculation:

For a 4 $\log_{10}$ reduction after 1 hours contact:

PAA=>80 (160)

DTEA=100 (200)

PAA/DTEA=40/12.5 40/160+12.50/200=0.3125=SI

For a 4 $\log_{10}$ reduction after 5 hours of contact:

PAA=80

DTEA=>100 (200)

PAA/DTEA=40/12.5 40/80+12.5/200=0.5625=SI

Example 12

Synergistic activity of peracetic acid and orthophthaldehyde (OPA) against microorganisms in paper mill service water, pH 7.0.

| Biocide (ppm product) | 150 min | 270 min | 24 Hours |
|---|---|---|---|
| PAA-40 | $2.3 \times 10^7$ | $2.6 \times 10^7$ | $1.5 \times 10^7$ |
| PAA-80 | $1.2 \times 10^7$ | $1.3 \times 10^7$ | $1.5 \times 10^7$ |
| PAA-160 | $4.2 \times 10^6$ | $3.8 \times 10^7$ | $1.7 \times 10^7$ |

| | 120 min | 240 min | 24 Hours |
|---|---|---|---|
| OPA-12.5 | $2.5 \times 10^6$ | $6.2 \times 10^5$ | $2.8 \times 10^7$ |
| OPA-25 | $2.7 \times 10^5$ | $2.1 \times 10^5$ | $1.7 \times 10^7$ |
| OPA-50 | $4.3 \times 10^4$ | $1.8 \times 10^4$ | $6.4 \times 10^6$ |
| OPA-100 | $1.5 \times 10^3$ | $9.5 \times 10^2$ | $3.4 \times 10^4$ |
| PAA-20/OPA-12.5 | $4.1 \times 10^5$ | $2.1 \times 10^6$ | $2.7 \times 10^7$ |
| PAA-20/OPA-25 | $9.7 \times 10^4$ | $1.3 \times 10^5$ | $1.9 \times 10^7$ |
| PAA-20/OPA-50 | $2.1 \times 10^3$ | $1.8 \times 10^3$ | $7.1 \times 10^6$ |
| PAA-20/OPA-100 | $7.2 \times 10^2$ | $<10^1$ | $4.8 \times 10^5$ |
| PAA-40/OPA-12.5 | $3.0 \times 10^5$ | $2.0 \times 10^5$ | $1.5 \times 10^7$ |
| PAA-40/OPA-25 | $5.4 \times 10^4$ | $8.9 \times 10^3$ | $5.2 \times 10^6$ |
| PAA-40/OPA-50 | $9.2 \times 10^2$ | $7.4 \times 10^2$ | $1.5 \times 10^7$ |
| PAA-40/OPA-100 | $6.4 \times 10^7$ | $6.2 \times 10^2$ | $5.3 \times 10^5$ |
| PAA-80/OPA-12.5 | $2.4 \times 10^5$ | $1.7 \times 10^5$ | $1.8 \times 10^7$ |
| PAA-80/OPA-25 | $3.1 \times 10^3$ | $4.4 \times 10^2$ | $3.1 \times 10^6$ |
| PAA-80/OPA-50 | $6.1 \times 10^2$ | $6.7 \times 10^2$ | $4.6 \times 10^3$ |
| PAA-80/OPA-100 | $7.4 \times 10^2$ | $5.3 \times 10^2$ | $3.5 \times 10^3$ |
| Control - 0 | $2.5 \times 10^7$ | $3.1 \times 10^7$ | $1.3 \times 10^7$ |

Synergy Calculation:
For a 4 $\log_{10}$ reduction after 24 hours contact:
PAA=>160 (320)
OPA=>100 (200)
PAA/OPA=80/50 80/320+50/200=0.5=SI
For a 4 $\log_{10}$ reduction after 5 hours of contact:
PAA=>160 (320)
OPA=100
PAA/OPA=80/12.5 80/320+12.5/100=0.375=SI

Example 13

Synergistic activity of peracetic acid and bromonitropropanediol (BNPD) against microorganisms in paper mill service water, pH 7.0.

| Biocide (ppm product) | 150 min | 270 min | 24 Hours |
|---|---|---|---|
| PAA-10 | $2.8 \times 10^6$ | $4.3 \times 10^6$ | $9.0 \times 10^6$ |
| PAA-20 | $1.6 \times 10^5$ | $1.3 \times 10^5$ | $1.5 \times 10^6$ |
| PAA-40 | $6.2 \times 10^3$ | $1.6 \times 10^3$ | $8.5 \times 10^4$ |

| | 120 min | 240 min | 24 Hours |
|---|---|---|---|
| BNPD-25 | $7.2 \times 10^6$ | $5.2 \times 10^6$ | $4.8 \times 10^4$ |
| BNPD-50 | $4.6 \times 10^6$ | $3.0 \times 10^6$ | $2.2 \times 10^4$ |
| BNPD-100 | $3.7 \times 10^6$ | $6.4 \times 10^5$ | $2.1 \times 10^3$ |
| BNPD-200 | $2.4 \times 10^6$ | $9.5 \times 10^4$ | $2.7 \times 10^2$ |
| PAA-5/BNPD-25 | $6.9 \times 10^6$ | $3.4 \times 10^6$ | $2.5 \times 10^6$ |
| PAA-5/BNPD-50 | $3.8 \times 10^6$ | $3.0 \times 10^6$ | $1.1 \times 10^5$ |
| PAA-5/BNPD-100 | $4.0 \times 10^6$ | $4.2 \times 10^5$ | $3.4 \times 10^3$ |
| PAA-5/BNPD-200 | $1.5 \times 10^6$ | $4.8 \times 10^5$ | $3.8 \times 10^2$ |
| PAA-10/BNPD-25 | $6.3 \times 10^5$ | $2.2 \times 10^5$ | $8.7 \times 10^4$ |
| PAA-10/BNPD-50 | $3.7 \times 10^5$ | $7.4 \times 10^4$ | $5.6 \times 10^4$ |
| PAA-10/BNPD-100 | $1.7 \times 10^5$ | $3.2 \times 10^4$ | $3.8 \times 10^4$ |
| PAA-10/BNPD-200 | $5.3 \times 10^4$ | $5.8 \times 10^2$ | $2.3 \times 10^2$ |
| PAA-20/BNPD-25 | $1.2 \times 10^5$ | $4.6 \times 10^3$ | $1.4 \times 10^3$ |
| PAA-20/BNPD-50 | $1.0 \times 10^5$ | $1.2 \times 10^3$ | $2.6 \times 10^2$ |
| PAA-20/BNPD-100 | $7.7 \times 10^4$ | $5.9 \times 10^2$ | $<10^1$ |
| PAA-20/BNPD-200 | $5.1 \times 10^4$ | $3.5 \times 10^2$ | $<10^1$ |
| Control - 0 | $7.9 \times 10^6$ | $9.2 \times 10^6$ | $6.5 \times 10^6$ |

Synergy Calculation:
For a 4 $\log_{10}$ reduction after 5 hours contact:
PAA=>40 (80)
N-7639=>200 (400)
PAA/N-7639=20/100 20/80+100/400=0.5=SI
For a 5 $\log_{10}$ reduction after 24 hours of contact:
PAA=>40 (80)
N-7639=>200 (400)
PAA/N-7639=20/100 20/80+100/400=0.5=SI

Example 14

Synergistic activity of peracetic acid and dichlorodithiol-3-one (RYH-86NA) against microorganisms in paper mill whitewater, pH=7.1.

| Biocide (ppm product) | 60 min | 240 min | 24 Hours |
|---|---|---|---|
| PAA-12.5 | $2.3 \times 10^6$ | $8.9 \times 10^6$ | $3.2 \times 10^6$ |
| PAA-25 | $2.7 \times 10^5$ | $3.7 \times 10^6$ | $1.0 \times 10^7$ |
| PAA-50 | $1.2 \times 10^4$ | $2.6 \times 10^4$ | $4.5 \times 10^7$ |

| | 30 min | 210 min | 24 Hours |
|---|---|---|---|
| RYH-86NA-5 | $2.6 \times 10^6$ | $3.6 \times 10^6$ | $1.5 \times 10^7$ |
| RYH-86NA-10 | $1.4 \times 10^5$ | $2.3 \times 10^4$ | $1.4 \times 10^7$ |
| RYH-86NA-20 | $2.3 \times 10^4$ | $4.2 \times 10^3$ | $4.0 \times 10^6$ |
| RYH-86NA-40 | $1.4 \times 10^4$ | $4.0 \times 10^3$ | $2.7 \times 10^3$ |
| PAA-10/RYH-86NA-5 | $1.9 \times 10^5$ | $4.0 \times 10^5$ | $2.9 \times 10^7$ |
| PAA-10/RYH-86NA-10 | $4.6 \times 10^3$ | $2.8 \times 10^3$ | $4.7 \times 10^6$ |
| PAA-10/RYH-86NA-20 | $2.7 \times 10^3$ | $3.0 \times 10^3$ | $2.6 \times 10^6$ |
| PAA-10/RYH-86NA-40 | $2.5 \times 10^4$ | $3.2 \times 10^3$ | $3.0 \times 10^3$ |
| PAA-20/RYH-86NA-5 | $2.3 \times 10^4$ | $3.6 \times 10^3$ | $2.7 \times 10^6$ |
| PAA-20/RYH-86NA-10 | $4.2 \times 10^3$ | $3.4 \times 10^3$ | $7.8 \times 10^6$ |
| PAA-20/RYH-86NA-20 | $3.1 \times 10^4$ | $3.6 \times 10^3$ | $3.1 \times 10^6$ |
| PAA-20/RYH-86NA-40 | $2.5 \times 10^4$ | $1.6 \times 10^4$ | $1.7 \times 10^4$ |
| PAA-40/RYH-86NA-5 | $2.7 \times 10^4$ | $4.1 \times 10^4$ | $1.9 \times 10^7$ |
| PAA-40/RYH-86NA-10 | $1.8 \times 10^4$ | $4.6 \times 10^4$ | $1.2 \times 10^7$ |
| PAA-40/RYH-86NA-20 | $2.4 \times 10^4$ | $1.8 \times 10^4$ | $1.4 \times 10^7$ |
| PAA-40/RYH-86NA-40 | $2.6 \times 10^4$ | $2.4 \times 10^4$ | $6.5 \times 10^6$ |
| Control - 0 | $3.5 \times 10^6$ | $1.9 \times 10^6$ | $3.4 \times 10^6$ |

Synergy Calculation
For a 3 $\log_{10}$ reduction after 4 hours contact:
PAA=>50 (100)
RYH-86NA=20
PAA/RYH-86NA=10/10 10/100+10/20=0.6=SI
PAA/RYH-86NA=20/5 20/100+5/20=0.45=SI

Example 15

Synergistic activity of peracetic acid and dichloro-n-octyl isothiazolin (RH-287) against bacteria in papermill whitewater, pH 7.1.

| Biocide (ppm product) | | | |
|---|---|---|---|
| | 60 min | 240 min | 24 Hours |
| PAA-12.5 | $3.1 \times 10^6$ | $5.4 \times 10^6$ | $3.9 \times 10^7$ |
| PAA-25 | $2.7 \times 10^5$ | $1.9 \times 10^6$ | $5.0 \times 10^7$ |
| PAA-50 | $1.3 \times 10^5$ | $8.4 \times 10^4$ | $7.8 \times 10^7$ |
| | 30 min | 210 min | 24 Hours |
| RH-287-25 | $4.6 \times 10^6$ | $1.5 \times 10^7$ | $6.4 \times 10^7$ |
| RH-287-50 | $4.1 \times 10^6$ | $1.2 \times 10^7$ | $3.6 \times 10^7$ |
| RH-287-100 | $4.6 \times 10^6$ | $2.3 \times 10^6$ | $2.8 \times 10^7$ |
| RH-287-200 | $3.9 \times 10^6$ | $1.1 \times 10^5$ | $2.6 \times 10^7$ |
| PAA-10/RH-287-25 | $3.8 \times 10^6$ | $5.4 \times 10^6$ | $5.8 \times 10^7$ |
| PAA-10/RH-287-50 | $3.4 \times 10^6$ | $2.0 \times 10^6$ | $3.8 \times 10^7$ |
| PAA-10/RH-287-100 | $2.1 \times 10^6$ | $1.3 \times 10^5$ | $2.4 \times 10^7$ |
| PAA-10/RH-287-200 | $7.3 \times 10^5$ | $2.0 \times 10^4$ | $2.3 \times 10^7$ |
| PAA-20/RH-287-25 | $5.1 \times 10^5$ | $4.8 \times 10^5$ | $6.3 \times 10^7$ |
| PAA-20/RH-287-50 | $4.4 \times 10^5$ | $1.8 \times 10^5$ | $6.1 \times 10^7$ |
| PAA-20/RH-287-100 | $3.2 \times 10^5$ | $5.0 \times 10^4$ | $3.5 \times 10^7$ |
| PAA-20/RH-287-200 | $1.2 \times 10^5$ | $7.3 \times 10^3$ | $2.3 \times 10^7$ |
| PAA-40/RH-287-25 | $2.3 \times 10^5$ | $7.1 \times 10^4$ | $6.1 \times 10^7$ |
| PAA-40/RH-287-50 | $2.1 \times 10^5$ | $4.0 \times 10^4$ | $6.2 \times 10^7$ |
| PAA-40/RH-287-100 | $1.5 \times 10^5$ | $2.3 \times 10^4$ | $4.7 \times 10^7$ |
| PAA-40/RH-287-200 | $2.0 \times 10^5$ | $1.9 \times 10^4$ | $2.0 \times 10^7$ |
| Control - 0 | $4.8 \times 10^6$ | $4.6 \times 10^6$ | $2.3 \times 10^7$ |

Synergy Calculation:
For a 3 $\log_{10}$ reduction after 4 hours contact:
PAA=>50 (100)
RH-287=>200 (400)
PAA/RH-287=20/200 20/100+200/400=0.7=SI

Example 16

Synergistic activity of peracetic acid and 1-(3-chloroallyl)-3,5,7-triaza-1-azoniaadamantane chloride (D75) against bacteria in papermill whitewater, pH 7.1.

| Biocide (ppm product) | | |
|---|---|---|
| | 60 min | 240 min |
| PAA-25 | $1.6 \times 10^5$ | $1.7 \times 10^5$ |
| PAA-50 | $1.4 \times 10^4$ | $2.0 \times 10^5$ |
| PAA-100 | $3.2 \times 10^3$ | $2.0 \times 10^2$ |
| | 30 min | 210 min |
| D75-50 | $4.0 \times 10^5$ | $7.2 \times 10^4$ |
| D75-100 | $3.7 \times 10^5$ | $6.7 \times 10^4$ |
| D75-200 | $2.9 \times 10^5$ | $6.0 \times 10^4$ |
| D75-400 | $3.5 \times 10^5$ | $6.3 \times 10^4$ |
| PAA-10/D75-50 | $2.4 \times 10^5$ | $9.9 \times 10^4$ |
| PAA-10/D75-100 | $2.1 \times 10^5$ | $5.8 \times 10^4$ |
| PAA-10/D75-200 | $1.6 \times 10^5$ | $2.5 \times 10^4$ |
| PAA-10/D75-400 | $1.9 \times 0^5$ | $2.8 \times 10^3$ |
| PAA-20/D75-50 | $2.1 \times 10^5$ | $1.1 \times 10^5$ |
| PAA-20/D75-100 | $2.6 \times 10^5$ | $8.7 \times 10^4$ |
| PAA-20/D75-200 | $2.6 \times 10^5$ | $1.6 \times 10^5$ |
| PAA-20/D75-400 | $2.2 \times 10^5$ | $8.2 \times 10^3$ |
| PAA-40/D75-50 | $1.9 \times 10^5$ | $8.1 \times 10^4$ |
| PAA-40/D75-100 | $2.0 \times 10^5$ | $1.1 \times 10^5$ |
| PAA-40/D75-200 | $1.8 \times 10^5$ | $5.2 \times 10^4$ |
| PAA-40/D75-400 | $1.6 \times 10^5$ | $6.5 \times 10^3$ |
| Control - 0 | $6.1 \times 10^5$ | $2.5 \times 10^6$ |

Synergy Calculation:
After 4 hours of contact, a 2 $\log_{10}$ reduction was achieved with:
PAA=100
D75=>400 (800)
PAA=10 ppm/D75=400 ppm
SI=10/100+400/800=0.60

Example 17

Synergistic activity of peracetic acid and bis (trichloromethyl) sulfone (BTCMS) against bacteria in paper mill whitewater, pH 7.1.

| Biocide (ppm product) | | | |
|---|---|---|---|
| | 60 min | 240 min | 24 Hours |
| PAA-25 | $7.0 \times 10^5$ | $8.0 \times 10^5$ | $1.7 \times 10^6$ |
| PAA-50 | $7.0 \times 10^5$ | $1.9 \times 10^6$ | $5.4 \times 10^6$ |
| PAA-100 | $8.0 \times 10^5$ | $8.1 \times 10^5$ | $9.6 \times 10^6$ |
| | 30 min | 210 min | 24 Hours |
| BTCMS-10 | $5.0 \times 10^5$ | $8.0 \times 10^4$ | $8.4 \times 10^6$ |
| BTCMS-20 | $1.1 \times 10^6$ | $1.2 \times 10^5$ | $9.2 \times 10^6$ |
| BTCMS-40 | $8.0 \times 10^5$ | $5.9 \times 10^4$ | $1.7 \times 10^6$ |
| BTCMS-80 | $1.1 \times 10^5$ | $4.6 \times 10^4$ | $1.3 \times 10^5$ |
| PAA-10/BTCMS-10 | $1.5 \times 10^6$ | $6.0 \times 10^5$ | $8.6 \times 10^6$ |
| PAA-10/BTCMS-20 | $4.0 \times 10^5$ | $6.5 \times 10^4$ | $4.6 \times 10^6$ |
| PAA-10/BTCMS-40 | $1.1 \times 10^5$ | $6.3 \times 10^3$ | $5.1 \times 10^4$ |
| PAA-10/BTCMS-80 | $5.1 \times 10^4$ | $4.7 \times 10^2$ | $4.5 \times 10^2$ |
| PAA-20/BTCMS-10 | $1.1 \times 10^5$ | $1.0 \times 10^5$ | $6.0 \times 10^6$ |
| PAA-20/BTCMS-20 | $3.0 \times 10^5$ | $1.1 \times 10^3$ | $1.1 \times 10^7$ |
| PAA-20/BTCMS-40 | $1.0 \times 10^5$ | $8.5 \times 10^2$ | $2.0 \times 10^6$ |
| PAA-20/BTCMS-80 | $2.6 \times 10^4$ | $6.0 \times 10^3$ | $1.2 \times 10^3$ |
| Control - 0 | $9.0 \times 10^5$ | $1.4 \times 10^6$ | $2.0 \times 10^6$ |

Synergy Calculation:
For a 3 $\log_{10}$ reduction after 4 hours contact:
PAA=>100 (200)
BTCMS=>80 (160)
PAA=10 ppm/BTCMS=40 ppm
SI=10/200+40/160=0.30
PAA=20 ppm/BTCMS=20 PPM
SI=20/200+20/160=0.225
For a 3 $\log_{10}$ reduction after 4 hours contact:
PAA=>100 (200)
BTCMS=>80 (160)
PAA=10 ppm/BTCMS=80 ppm
SI=10/200+80/160=0.55
PAA=20 ppm/BTCMS=80 PPM
SI=20/200+80/160=0.60

Example 18

Synergy Study: Combination of Peracetic acid (PAA) and Isothiazolinone

Organism Used: *Pseudomonas aeruginosa* (PA01), typical cooling water bacterium

Water used: Synthetic cooling water (standard no. 13, adjusted to pH of 7.0)

| | Time = 0 CFU/ML | Time = 17 hours CFU/ML |
|---|---|---|
| Control (No added biocide) | 9.3 e6 | 2.0 e7 |
| Peracetic Acid (PAA) - only | | |
| 4 ppm as product | | 2.7 e7 |
| 8 ppm as product | | 1.5 e6 |
| 16 ppm as product | | 4.7 e4 |

-continued

| | Time = 0 CFU/ML | Time = 17 hours CFU/ML |
|---|---|---|
| 32 ppm as product | | 4.7 e3 |
| 40 ppm as product | | 2.0 e2 |
| Isothiazolinone - only | | |
| 10 ppm as product | | 5.7 e6 |
| 20 ppm as product | | 1.0 e6 |
| 40 ppm as product | | 1.0 e6 |
| 50 ppm as product | | 6.4 e5 |
| 75 ppm as product | | 7.7 e4 |
| 100 ppm as product | | 4.0 e3 |
| Peracetic acid (5 ppm as product) + Isothiazolinone | | |
| 10 ppm as product | | 2.3 e5 |
| 20 ppm as product | | 1.0 e5 |
| 40 ppm as product | | 3.0.e3 |
| 50 ppm as product | | 2.7 e3 |
| 75 ppm as product | | 1.2 e3 |
| 100 ppm as product | | 4.0 e2 |
| Peracetic acid (10 ppm as product) + Isothiazolinone | | |
| 10 ppm as product | | 5.4 e4 |
| 20 ppm as product | | 4.4 e3 |
| 40 ppm as product | | 5.7 e3 |
| 50 ppm as product | | 7.2 e2 |
| 75 ppm as product | | 1.0 e2 |
| 100 ppm as product | | 4.8 e2 |

Synergy Index:(5 ppm PAA + 40 ppm Isothazolinone: 0.125 + 0.5 = 0.525 (<1.0), Synergistic Example 19

Synergistic activity of peracetic acid and 1-(3-chloroallyl)-3,5,7-triaza-1-azoniaadamantane chloride (D75) against bacteria in a 55% solids Kaolin clay slurry, pH 8.3.

| Biocide (ppm product) | 1 Day | 1 Week | 4 Weeks |
|---|---|---|---|
| PAA-500 | $6.0 \times 10^5$ | $3.1 \times 10^7$ | $>10^7$ |
| PAA-1000 | $<10^3$ | $5.0 \times 10^7$ | $>10^7$ |
| PAA-2000 | $5.8 \times 10^6$ | $9.8 \times 10^7$ | $>10^7$ |
| D75-250 | $<10^3$ | $<10^3$ | $>10^7$ |
| D75-500 | $<10^3$ | $<10^3$ | $2 \times 10^3$ |
| D75-1000 | $<10^3$ | $<10^3$ | $3 \times 10^3$ |
| PAA-500/D75-500 | $<10^3$ | $<10^3$ | $<10^3$ |
| Control - 0 | $9.7 \times 10^4$ | $>10^7$ | $>10^7$ |

Synergy Calculation:

To achieve an endpoint of $<10^3$ CFU/mL for 4 weeks of contact:

PAA=>2000 ppm (4000)
D75=>1000 ppm (2000)
PAA=500/D75 =500
SI=500/4000+500/2000=0.375

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims:

We claim:

1. A composition for inhibiting the growth of microorganisms in aqueous systems comprising effective amounts of peracetic acid and a non-oxidizing biocide selected from the group consisting of: decylthioethylamine, orthophthaldehyde, dodecylguanidine hydrochloride, 1-(3-chloroallyl)-3,5,7-triaza-1-azoniaadamantane chloride, dibromo dicyanobutane and bis(trichloromethyl)sulfone, said amount of peracetic acid and non-oxidizing biocide being selected to result in a synergy index of less than 1 wherein said synergy index is calculated by determining a first ratio of the amount of peracetic acid required to produce a level of microorganism growth inhibition when added in combination with the amount of non-oxidizing biocide to the amount of peracetic acid required to produce the level of growth inhibition in the absence of the non-oxidizing biocide, and adding the first ratio to a second ratio of the amount of non-oxidizing biocide required to produce the level of growth inhibition when added in combination with the amount of peracetic acid to the amount of non-oxidizing biocide required to produce the level of growth inhibition in the absence of the peracetic acid.

2. The composition of claim 1 wherein the amount of peracetic acid ranges from approximately 5 to 250 ppm and the amount of non-oxidizing biocide ranges from approximately 10 to 250 ppm.

3. A method for controlling the growth of microorganisms in industrial process water including the step of administering a sufficient amount of a peracetic acid and a sufficient amount of a non-oxidizing biocide to the industrial process water to inhibit the growth of the microorganisms, said non-oxidizing biocide selected from the group consisting of decylthioethylamine, orthophthaldehyde, dodecylguanidine hydrochloride, 1-(3-chloroallyl)-3,5,7-triaza-1-azoniaadamantane chloride, dibromo dicyanobutane and bis(trichloromethyl)sulfone, said non-oxidizing biocide being selected to result in a synergy index of less than 1 wherein said synergy index is calculated by determining a first ratio of the amount of peracetic acid required to produce a level of microorganism growth inhibition when added in combination with the amount of non-oxidizing biocide to the amount of peracetic acid required to produce the level of growth inhibition in the absence of the non-oxidizing biocide, and adding the first ratio to a second ratio of the amount of non-oxidizing biocide required to produce the level of growth inhibition when added in combination with the amount of peracetic acid to the amount of non-oxidizing biocide required to produce the level of growth inhibition in the absence of the peracetic acid.

4. The method of claim 3 wherein the industrial process water is selected from the group consisting of water of a pulp and paper mill system, cooling water and mining.

5. The method of claim 3 wherein the peracetic acid and the non-oxidizing biocide are added in a ratio from about 10:1 to 1:25.

6. The method of claim 3 wherein the amount of peracetic acid added ranges from approximately 5 to 250 ppm and the non-oxidizing biocide ranges from approximately 10 to 250 ppm.

7. The method of claim 3 wherein the microorganisms contain bacteria.

8. The method of claim 3 wherein the microorganisms contain fungi.

9. The method of claim 3 wherein the peracetic acid is added to the industrial water prior to the addition of the non-oxidizing biocide.

* * * * *